(12) United States Patent
Deubzer et al.

(10) Patent No.: US 8,361,955 B2
(45) Date of Patent: Jan. 29, 2013

(54) METHODS FOR TREATING AND PREVENTING BRAIN TUMORS BASED ON BONE MORPHOGENETIC PROTEINS

(75) Inventors: Hedwig Elisabeth Deubzer, Heidelberg (DE); Olaf Witt, Schriesheim (DE)

(73) Assignee: DKFZ Deutsches Krebsforschungszentrum, Stiftung des Offentlichen Rechts, Heidelberg (DE)

( * ) Notice: Subject to any disclaimer, the term of this patent is extended or adjusted under 35 U.S.C. 154(b) by 150 days.

(21) Appl. No.: 12/867,441

(22) PCT Filed: Feb. 4, 2009

(86) PCT No.: PCT/EP2009/051258
§ 371 (c)(1),
(2), (4) Date: Aug. 12, 2010

(87) PCT Pub. No.: WO2009/101012
PCT Pub. Date: Aug. 20, 2009

(65) Prior Publication Data
US 2011/0020334 A1    Jan. 27, 2011

Related U.S. Application Data

(60) Provisional application No. 61/028,371, filed on Feb. 13, 2008.

(51) Int. Cl.
*A61K 38/00* (2006.01)
(52) U.S. Cl. ...................................................... 514/1.1
(58) Field of Classification Search .................. None
See application file for complete search history.

(56) References Cited

U.S. PATENT DOCUMENTS 5,693,615 A * 12/1997 Stone .............................. 514/8.8
6,949,505 B1     9/2005 Rueger et al.

FOREIGN PATENT DOCUMENTS
WO    WO 2007/010394 A2    1/2007

OTHER PUBLICATIONS

Thomas et al., Nature Reviews Genetics, 2003, 4: 346-358.*
Bangari et al., Curr. Gene. Ther., 2006, 6:215-226.*
Goncalves et al., Bioessays, 2005, 27: 506-517.*
Bowie, et al. Science, vol. 247: 1306-1310, 1990.*
Lazar, et al. Mol. Cell. Biol., 8(3): 1247-1252, 1988.*
Burgess, et al. J. Cell Biol. 111: 2129-2138, 1990.*
Ngo et al., in"The Protein Folding Problem and Tediary Structure Prediction", 1994, Merz, et al. (ed.), Birkhauser, Boston, MA, pp. 433, and 492-495.*
Berthold et al., "Long-term results and risk profiles of patients in five consecutive trials (1979-1997) with stage 4 neuroblastoma over 1 year of age," Cancer Letters, vol. 197, 2003, pp. 11-17.
Matthay et al., "Treatment of High-Risk Neuroblastoma with Intensive Chemotherapy, Radiotherapy, Autologous Bone Marrow Transplantation, and 13-CIS-Retinoic Acid," The New England Journal of Medicine, vol. 341, No. 16, Oct. 14, 1999, pp. 1165-1173.
Nakamura et al., "Accumulation of p27KIP1 is associated with BMP2-induced growth arrest and neuronal differentiation of human neuroblastoma-derived cell lines," Biochemical and Biophysical Research Communications, vol. 307, 2003, pp. 206-213.
Piccirillo et al., "Bone morhogenetic proteins inhibit the tumorigenic potential of human brain tumour-initiating cells," Nature, vol. 444, Dec. 7, 2006, pp. 761-765, XP-002526801.

* cited by examiner

*Primary Examiner* — Hong Sang
(74) *Attorney, Agent, or Firm* — Birch, Stewart, Kolasch & Birch, LLP

(57) ABSTRACT

The present invention is concerned with the therapy of neuroblastoma and related diseases. Specifically, the present invention relates to a method for treating or preventing neuroblastoma comprising administering to a subject a therapeutically effective amount of bone morphogenetic protein 4 (BMP4). Preferably, said BMP4 is applied together with chemotherapy and/or radiation therapy.

6 Claims, 1 Drawing Sheet

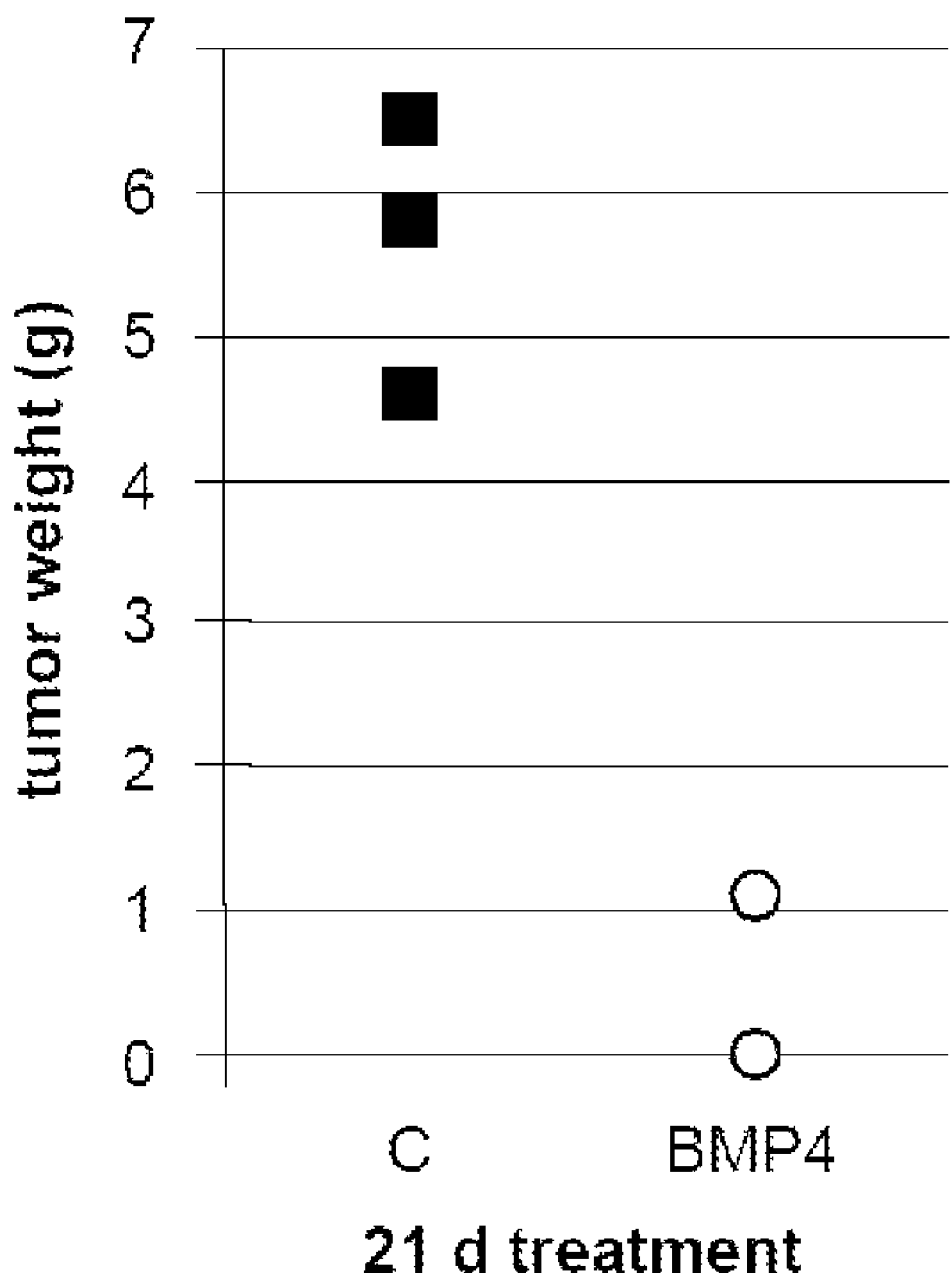

SEQUENCE LISTING

<160> NUMBER OF SEQ ID NOS: 2

<210> SEQ ID NO 1
<211> LENGTH: 1957
<212> TYPE: DNA
<213> ORGANISM: Homo sapiens
<220> FEATURE:
<221> NAME/KEY: CDS
<222> LOCATION: (420)..(1646)

<400> SEQUENCE: 1

| | |
|---|---:|
| aagaggagga aggaagatgc gagaaggcag aggaggaggg agggagggaa ggagcgcgga | 60 |
| gcccggcccg gaagctaggt gagtgtggca tccgagctga gggacgcgag cctgagacgc | 120 |
| cgctgctgct ccggctgagt atctagcttg tctccccgat gggattcccg tccaagctat | 180 |
| ctcgagcctg cagcgccaca gtccccggcc ctcgcccagg ttcactgcaa ccgttcagag | 240 |
| gtccccagga gctgctgctg gcgagcccgc tactgcaggg acctatggag ccattccgta | 300 |
| gtgccatccc gagcaacgca ctgctgcagc ttccctgagc cttttccagca agtttgttca | 360 |
| agattggctg tcaagaatca tggactgtta ttatatgcct tgtttctgt caagacacc | 419 |

| atg att cct ggt aac cga atg ctg atg gtc gtt tta tta tgc caa gtc | 467 |
|---|---:|
| Met Ile Pro Gly Asn Arg Met Leu Met Val Val Leu Leu Cys Gln Val | |
| 1               5               10              15              | |

| ctg cta gga ggc gcg agc cat gct agt ttg ata cct gag acg ggg aag | 515 |
|---|---:|
| Leu Leu Gly Gly Ala Ser His Ala Ser Leu Ile Pro Glu Thr Gly Lys | |
|        20              25              30                      | |

| aaa aaa gtc gcc gag att cag ggc cac gcg gga gga cgc cgc tca ggg | 563 |
|---|---:|
| Lys Lys Val Ala Glu Ile Gln Gly His Ala Gly Gly Arg Arg Ser Gly | |
|    35              40              45                          | |

| cag agc cat gag ctc ctg cgg gac ttc gag gcg aca ctt ctg cag atg | 611 |
|---|---:|
| Gln Ser His Glu Leu Leu Arg Asp Phe Glu Ala Thr Leu Leu Gln Met | |
| 50              55              60                             | |

| ttt ggg ctg cgc cgc cgc ccg cag cct agc aag agt gcc gtc att ccg | 659 |
|---|---:|
| Phe Gly Leu Arg Arg Arg Pro Gln Pro Ser Lys Ser Ala Val Ile Pro | |
| 65              70              75              80             | |

| gac tac atg cgg gat ctt tac cgg ctt cag tct ggg gag gag gag gaa | 707 |
|---|---:|
| Asp Tyr Met Arg Asp Leu Tyr Arg Leu Gln Ser Gly Glu Glu Glu Glu | |
|            85              90              95                  | |

| gag cag atc cac agc act ggt ctt gag tat cct gag cgc ccg gcc agc | 755 |
|---|---:|
| Glu Gln Ile His Ser Thr Gly Leu Glu Tyr Pro Glu Arg Pro Ala Ser | |
|        100             105             110                     | |

| cgg gcc aac acc gtg agg agc ttc cac cac gaa gaa cat ctg gag aac | 803 |
|---|---:|
| Arg Ala Asn Thr Val Arg Ser Phe His His Glu Glu His Leu Glu Asn | |
|    115             120             125                         | |

| atc cca ggg acc agt gaa aac tct gct ttt cgt ttc ctc ttt aac ctc | 851 |
|---|---:|
| Ile Pro Gly Thr Ser Glu Asn Ser Ala Phe Arg Phe Leu Phe Asn Leu | |
| 130             135             140                            | |

| agc agc atc cct gag aac gag gtg atc tcc tct gca gag ctt cgg ctc | 899 |
|---|---:|
| Ser Ser Ile Pro Glu Asn Glu Val Ile Ser Ser Ala Glu Leu Arg Leu | |
| 145             150             155             160            | |

| ttc cgg gag cag gtg gac cag ggc cct gat tgg gaa agg ggc ttc cac | 947 |
|---|---:|
| Phe Arg Glu Gln Val Asp Gln Gly Pro Asp Trp Glu Arg Gly Phe His | |
|            165             170             175                 | |

| cgt ata aac att tat gag gtt atg aag ccc cca gca gaa gtg gtg cct | 995 |
|---|---:|
| Arg Ile Asn Ile Tyr Glu Val Met Lys Pro Pro Ala Glu Val Val Pro | |
|        180             185             190                     | |

| ggg cac ctc atc aca cga cta ctg gac acg aga ctg gtc cac cac aat | 1043 |
|---|---:|
| Gly His Leu Ile Thr Arg Leu Leu Asp Thr Arg Leu Val His His Asn | |
|    195             200             205                         | |

-continued

| | | | | | | | | | | | | | | | | |
|---|---|---|---|---|---|---|---|---|---|---|---|---|---|---|---|---|
| gtg | aca | cgg | tgg | gaa | act | ttt | gat | gtg | agc | cct | gcg | gtc | ctt | cgc | tgg | 1091 |
| Val | Thr | Arg | Trp | Glu | Thr | Phe | Asp | Val | Ser | Pro | Ala | Val | Leu | Arg | Trp | |
| | 210 | | | | 215 | | | | | 220 | | | | | | |

| | | | | | | | | | | | | | | | | |
|---|---|---|---|---|---|---|---|---|---|---|---|---|---|---|---|---|
| acc | cgg | gag | aag | cag | cca | aac | tat | ggg | cta | gcc | att | gag | gtg | act | cac | 1139 |
| Thr | Arg | Glu | Lys | Gln | Pro | Asn | Tyr | Gly | Leu | Ala | Ile | Glu | Val | Thr | His | |
| 225 | | | | | 230 | | | | | 235 | | | | | 240 | |

| | | | | | | | | | | | | | | | | |
|---|---|---|---|---|---|---|---|---|---|---|---|---|---|---|---|---|
| ctc | cat | cag | act | cgg | acc | cac | cag | ggc | cag | cat | gtc | agg | att | agc | cga | 1187 |
| Leu | His | Gln | Thr | Arg | Thr | His | Gln | Gly | Gln | His | Val | Arg | Ile | Ser | Arg | |
| | | | | 245 | | | | | 250 | | | | | 255 | | |

| | | | | | | | | | | | | | | | | |
|---|---|---|---|---|---|---|---|---|---|---|---|---|---|---|---|---|
| tcg | tta | cct | caa | ggg | agt | ggg | aat | tgg | gcc | cag | ctc | cgg | ccc | ctc | ctg | 1235 |
| Ser | Leu | Pro | Gln | Gly | Ser | Gly | Asn | Trp | Ala | Gln | Leu | Arg | Pro | Leu | Leu | |
| | | | 260 | | | | | 265 | | | | | 270 | | | |

| | | | | | | | | | | | | | | | | |
|---|---|---|---|---|---|---|---|---|---|---|---|---|---|---|---|---|
| gtc | acc | ttt | ggc | cat | gat | ggc | cgg | ggc | cat | gcc | ttg | acc | cga | cgc | cgg | 1283 |
| Val | Thr | Phe | Gly | His | Asp | Gly | Arg | Gly | His | Ala | Leu | Thr | Arg | Arg | Arg | |
| | | 275 | | | | | 280 | | | | | 285 | | | | |

| | | | | | | | | | | | | | | | | |
|---|---|---|---|---|---|---|---|---|---|---|---|---|---|---|---|---|
| agg | gcc | aag | cgt | agc | cct | aag | cat | cac | tca | cag | cgg | gcc | agg | aag | aag | 1331 |
| Arg | Ala | Lys | Arg | Ser | Pro | Lys | His | His | Ser | Gln | Arg | Ala | Arg | Lys | Lys | |
| | 290 | | | | | 295 | | | | | 300 | | | | | |

| | | | | | | | | | | | | | | | | |
|---|---|---|---|---|---|---|---|---|---|---|---|---|---|---|---|---|
| aat | aag | aac | tgc | cgg | cgc | cac | tcg | ctc | tat | gtg | gac | ttc | agc | gat | gtg | 1379 |
| Asn | Lys | Asn | Cys | Arg | Arg | His | Ser | Leu | Tyr | Val | Asp | Phe | Ser | Asp | Val | |
| 305 | | | | | 310 | | | | | 315 | | | | | 320 | |

| | | | | | | | | | | | | | | | | |
|---|---|---|---|---|---|---|---|---|---|---|---|---|---|---|---|---|
| ggc | tgg | aat | gac | tgg | att | gtg | gcc | cca | cca | ggc | tac | cag | gcc | ttc | tac | 1427 |
| Gly | Trp | Asn | Asp | Trp | Ile | Val | Ala | Pro | Pro | Gly | Tyr | Gln | Ala | Phe | Tyr | |
| | | | | 325 | | | | | 330 | | | | | 335 | | |

| | | | | | | | | | | | | | | | | |
|---|---|---|---|---|---|---|---|---|---|---|---|---|---|---|---|---|
| tgc | cat | ggg | gac | tgc | ccc | ttt | cca | ctg | gct | gac | cac | ctc | aac | tca | acc | 1475 |
| Cys | His | Gly | Asp | Cys | Pro | Phe | Pro | Leu | Ala | Asp | His | Leu | Asn | Ser | Thr | |
| | | | 340 | | | | | 345 | | | | | 350 | | | |

| | | | | | | | | | | | | | | | | |
|---|---|---|---|---|---|---|---|---|---|---|---|---|---|---|---|---|
| aac | cat | gcc | att | gtg | cag | acc | ctg | gtc | aat | tct | gtc | aat | tcc | agt | atc | 1523 |
| Asn | His | Ala | Ile | Val | Gln | Thr | Leu | Val | Asn | Ser | Val | Asn | Ser | Ser | Ile | |
| | | 355 | | | | | 360 | | | | | 365 | | | | |

| | | | | | | | | | | | | | | | | |
|---|---|---|---|---|---|---|---|---|---|---|---|---|---|---|---|---|
| ccc | aaa | gcc | tgt | tgt | gtg | ccc | act | gaa | ctg | agt | gcc | atc | tcc | atg | ctg | 1571 |
| Pro | Lys | Ala | Cys | Cys | Val | Pro | Thr | Glu | Leu | Ser | Ala | Ile | Ser | Met | Leu | |
| | 370 | | | | | 375 | | | | | 380 | | | | | |

| | | | | | | | | | | | | | | | | |
|---|---|---|---|---|---|---|---|---|---|---|---|---|---|---|---|---|
| tac | ctg | gat | gag | tat | gat | aag | gtg | gta | ctg | aaa | aat | tat | cag | gag | atg | 1619 |
| Tyr | Leu | Asp | Glu | Tyr | Asp | Lys | Val | Val | Leu | Lys | Asn | Tyr | Gln | Glu | Met | |
| 385 | | | | | 390 | | | | | 395 | | | | | 400 | |

| | | | | | | | | |
|---|---|---|---|---|---|---|---|---|
| gta | gta | gag | gga | tgt | ggg | tgc | cgc | tga gatcaggcag tccttgagga | 1666 |
| Val | Val | Glu | Gly | Cys | Gly | Cys | Arg | | |
| | | | | 405 | | | | | | tagacagata tacacaccac acacacacac cacatacacc acacacacac gttcccatcc    1726 actcacccac acactacaca gactgcttcc ttatagctgg actttatttt aaaaaaaaaa    1786 aaaaaaaagg aaaaaatccc taaacattca ccttgacctt atttatgact ttacgtgcaa    1846 atgttttgac catattgatc atatattttg acaaaatata tttataacta cgtattaaaa    1906 gaaaaaaata aaatgagtca ttattttaaa ggtaaaaaaa aaaaaaaaaa a             1957

<210> SEQ ID NO 2
<211> LENGTH: 408
<212> TYPE: PRT
<213> ORGANISM: Homo sapiens

<400> SEQUENCE: 2

Met Ile Pro Gly Asn Arg Met Leu Met Val Val Leu Leu Cys Gln Val
1               5                   10                  15

Leu Leu Gly Gly Ala Ser His Ala Ser Leu Ile Pro Glu Thr Gly Lys
            20                  25                  30

Lys Lys Val Ala Glu Ile Gln Gly His Ala Gly Gly Arg Arg Ser Gly
        35                  40                  45

-continued

```
Gln Ser His Glu Leu Leu Arg Asp Phe Glu Ala Thr Leu Leu Gln Met
    50                      55                  60
Phe Gly Leu Arg Arg Arg Pro Gln Pro Ser Lys Ser Ala Val Ile Pro
65                  70                  75                  80
Asp Tyr Met Arg Asp Leu Tyr Arg Leu Gln Ser Gly Glu Glu Glu Glu
            85                  90                  95
Glu Gln Ile His Ser Thr Gly Leu Glu Tyr Pro Glu Arg Pro Ala Ser
            100                 105                 110
Arg Ala Asn Thr Val Arg Ser Phe His His Glu Glu His Leu Glu Asn
            115                 120                 125
Ile Pro Gly Thr Ser Glu Asn Ser Ala Phe Arg Phe Leu Phe Asn Leu
    130                 135                 140
Ser Ser Ile Pro Glu Asn Glu Val Ile Ser Ser Ala Glu Leu Arg Leu
145                 150                 155                 160
Phe Arg Glu Gln Val Asp Gln Gly Pro Asp Trp Glu Arg Gly Phe His
                165                 170                 175
Arg Ile Asn Ile Tyr Glu Val Met Lys Pro Pro Ala Glu Val Val Pro
            180                 185                 190
Gly His Leu Ile Thr Arg Leu Leu Asp Thr Arg Leu Val His His Asn
            195                 200                 205
Val Thr Arg Trp Glu Thr Phe Asp Val Ser Pro Ala Val Leu Arg Trp
    210                 215                 220
Thr Arg Glu Lys Gln Pro Asn Tyr Gly Leu Ala Ile Glu Val Thr His
225                 230                 235                 240
Leu His Gln Thr Arg Thr His Gln Gly Gln His Val Arg Ile Ser Arg
                245                 250                 255
Ser Leu Pro Gln Gly Ser Gly Asn Trp Ala Gln Leu Arg Pro Leu Leu
            260                 265                 270
Val Thr Phe Gly His Asp Gly Arg Gly His Ala Leu Thr Arg Arg Arg
            275                 280                 285
Arg Ala Lys Arg Ser Pro Lys His His Ser Gln Arg Ala Arg Lys Lys
    290                 295                 300
Asn Lys Asn Cys Arg Arg His Ser Leu Tyr Val Asp Phe Ser Asp Val
305                 310                 315                 320
Gly Trp Asn Asp Trp Ile Val Ala Pro Pro Gly Tyr Gln Ala Phe Tyr
                325                 330                 335
Cys His Gly Asp Cys Pro Phe Pro Leu Ala Asp His Leu Asn Ser Thr
            340                 345                 350
Asn His Ala Ile Val Gln Thr Leu Val Asn Ser Val Asn Ser Ser Ile
            355                 360                 365
Pro Lys Ala Cys Cys Val Pro Thr Glu Leu Ser Ala Ile Ser Met Leu
    370                 375                 380
Tyr Leu Asp Glu Tyr Asp Lys Val Val Leu Lys Asn Tyr Gln Glu Met
385                 390                 395                 400
Val Val Glu Gly Cys Gly Cys Arg
                405
```

METHODS FOR TREATING AND PREVENTING BRAIN TUMORS BASED ON BONE MORPHOGENETIC PROTEINS

CROSS REFERENCE TO RELATED APPLICATIONS

This application is the National Phase of PCT/EP2009/051258 filed on Feb. 4, 2009, which claims priority under 35 U.S.C. 119(e) to U.S. Provisional Application No. 61/028,371 filed on Feb. 13, 2008, all of which are hereby expressly incorporated by reference into the present application.

The present invention is concerned with the therapy of neuroblastoma and related diseases. Specifically, the present invention relates to a method for treating or preventing neuroblastoma comprising administering to a subject a therapeutically effective amount of bone morphogenetic protein 4 (BMP4). Preferably, said BMP4 is applied together with chemotherapy and/or radiation therapy.

The pediatric neuroblastoma in its advanced stage (stage 1V) is usually lethal. Although chemotherapy, surgery and radiation are available, statistically, some 70% of the affected children die. The therapies available so far often are accompanied with severe side effects resulting in lethality.

The current therapy of neuroblastoma pivotally comprises chemotherapy, radiation therapy, surgery, radionuclear therapeutic approaches as well as antibody or retinoic acid based therapies. In 70% to 90% of the cases, using a risk adopted therapeutic approach, localized stages of the diseases may be either treated by surgery alone or by a combination of surgery and radiation (Berthold, 2003, Cancer Lett 197: 11-17). Half of the children suffering from neuroblastoma, however, show upon diagnosis metastasis or a genetic amplification of the MYCNN oncogene. This group of patients has a poor prognosis and a (5 year period) survival rate of merely 33% even though treated by multiple approaches, such as surgery, chemotherapy, high dosage chemotherapy including stem cell transplantation, radiation, iodine-131 metaiodobenzylguanidine ($^{131}$I-MIBG) therapy and anti-GD2 antibody therapy (Berthold loc. cit.). However, administration of the differentiation inducing agent retinoic acid could somewhat improve the prognosis for the patients of the risk group mentioned above (Matthay 1999, N Engl J Med 341: 1165-1173). BMP2, a member of the TGF-beta family of growth and differentiation factors, has been reported to induce growth arrest and neuronal differentiation in neuroblastoma-derived cell lines (Nakamura 2003, Biochemical and Biophysical Research Communications 307: 206-213).

A drawback of the current standard therapy for high risk neuroblastoma using surgery, chemotherapy, high dosage chemotherapy including stem cell transplantation, radiation and $^{131}$I-MIBG therapy is the poor efficacy accompanied by the high lethality rate of approx. 70%. Moreover, serious side effects have been regularly encountered including toxicity for the mucous membranes, damages of kidney, inner ear and heart as well as, most importantly, severe bone marrow depression resulting in the need of frequent transfusions and in fulminant infections leading to lethal sepsis.

Accordingly, there is a need for means and methods for reliably preventing or treating neuroblastoma and related diseases.

Thus, the present invention relates to a method for treating or preventing neuroblastoma comprising administering to a subject a therapeutically effective amount of bone morphogenetic protein 4 (BMP4).

The term "treating" as used herein refers to removing the neuroblastoma from the subject or at least ameliorating the neuroblastoma in size, weight or aggressiveness (i.e. abolishing further growth or progression from a benign to a malign stage). Moreover, the term also includes ameliorating the symptoms associated with the said neuroblastoma. It is to be understood that treatment will not be necessarily achieved in all (100%) of the subjects of a population to be treated. However, it is envisaged that at least a statistically significant portion of the subjects of a population can be treated. Whether a portion is statistically significant can be determined without further ado by the person skilled in the art using various well known statistic evaluation tools, e.g., determination of confidence intervals, p-value determination, Student's t-test, Mann-Whitney test etc. Preferred confidence intervals are at least 90%, at least 95%, at least 97%, at least 98% or at least 99%. The p-values are, preferably, 0.1, 0.05, 0.01, 0.005, or 0.0001. More preferably, it is envisaged that treatment occurs in at least the $75^{th}$ percentile, at least the $80^{th}$ percentile, at least the $90^{th}$ percentile.

The term "preventing" as used herein refers to abolishing the de novo formation of neuroblastoma or the progression of an existing neuroblastoma. It is to be understood that prevention will not be necessarily achieved in all (100%) of the subjects of a population. However, it is envisaged that prevention occurs in at least a statistically significant portion of the subjects of a population. Whether a portion is statistically significant can be determined without further ado by the person skilled in the art using various well known statistic evaluation tools described above.

The term "neuroblastoma" encompasses all kinds of neuroblastomas. Specifically, all stages of a neuroblastoma are comprised by the term. Staging is carried out, preferably, according to the International Neuroblastoma Staging System (INSS) (Brodeur 1993, J Clin Oncol 11: 1466-1477). In principle, this surgical based staging distinguishes 5 basic stages of neuroblastoma: Stage I: Localized tumour confined to the area of origin. Complete gross resection with or without microscopic residual disease; identifiable ipsilateral and contralateral lymph node negative for tumour. Stage II: Unilateral tumour with incomplete gross resection; identifiable ipsilateral and contralateral lymph node negative for tumour (stage II a), with ipsilateral lymph node positive for tumour, identifiable contralateral lymph node negative for tumour (stage II b). Stage III: Tumour infiltrating across the midline with or without regional lymph node involvement; or unilateral tumour with contralateral lymph node involvement or midline tumour with bilateral lymph node involvement. Stage IV: Dissemination of tumour to distant lymph nodes, bone marrow, liver, or other organs except as defined in stage IVS. Stage IVS: Localized primary tumour as defined for stage 1 or 2 with dissemination limited to liver, skin, and bone marrow (<10% of nucleated marrow cells are tumor cells). Preferably, neuroblastomas as referred to herein are pediatric or childhood neuroblastomas which are in an advanced stage, i.e. stage IV. More preferably, the neuroblastomas to be treated in accordance with the use of the present invention are stage IV neuroblastomas or neuroblastomas having the MYCN oncogene amplified, most preferably stage IV neuroblastomas having the MYCN oncogene amplified. Whether a subject suffers from any one of the aforementioned neuroblastomas can be diagnosed by techniques well known in the art. For example, the neuroblastomas may be diagnosed based on accompanying symptoms which are described above. The following tests and procedures may be used to determine the stage: Bone marrow aspiration and biopsy: The removal of a small piece of bone and bone marrow by inserting a needle into the hipbone or tibia. A pathologist views both the bone and the bone marrow samples under a microscope to look for signs of cancer. Tumour and lymph node biopsy: The removal of all or part of a tumour or lymph node. A pathologist views the tissue under a microscope to look for cancer cells. One of the following types of biopsies may be done: Excisional biopsy, i.e. removal of an entire tumour or lymph node; Incisional biopsy or core biopsy, i.e. removal of part of a tumour or lymph node using a wide needle; Needle biopsy or fine-needle aspiration, i.e. removal of a sample of tissue or fluid from a tumour or lymph node using a thin needle; CT scan (CAT scan); MRI (magnetic resonance imaging) sometimes also called nuclear magnetic resonance imaging (NMRI); X-rays of the chest, bones, and abdomen; Ultrasound (sonogram); or Radionuclide scan: A procedure to find areas in the body where cells, such as cancer cells, are dividing rapidly. A very small amount of radioactive material is swallowed or injected into a vein and travels through the bloodstream. The radioactive material collects in the bones or other tissues and is detected by a radiation-measuring device. Given the strong association between MYCN oncogene amplification and poor clinical outcome, determination of MYCN oncogene status in neuroblastoma tumours prior to starting therapy has become an international standard and can be carried out as described in (Schwab 2003, Lancet Oncol, 4: 472-480. The MYCN amplification can be determined by standard molecular biology techniques such as PCR-based assays. The MYCN oncogene referred to herein is, preferably, the MYCNN oncogene.

The term subject as used herein, preferably, refers to a mammal and, more preferably, to a human.

The term "bone morphogenetic protein 4 (BMP4)" refers to a growth factor or cytokine of the TGF-beta family of growth factors which was originally due to its role in bone and cartilage formation as well as mesoderm patterning. BMP4 is transcribed as a preproprotein. The biologically active mature BMP4 is generated by proteolytic cleavage of from the said preproprotein. BMP4 as used encompasses to the mature BMP4 as well as to the proprotein or the preproprotein. The structure of BMP4 proteins from various species are well known in the art (Di Chen 2004, Growth Factors 22(4): 233-241; Granjeiro 2005, Brazilian Journal of Medical and Biological Research 38: 1463-1473; Leong 1996, Int J Biochem Cell Biol 28(12): 1293-1269). Preferably, BMP4 in accordance with the present invention BMP4 refers to human BMP4 as deposited in the NCBI database under accession numbers NM_001202.3 (GI:15727659), NM_130850.2 (GI:157276594) or NM_130851.2 (GI:157276596) or as having an amino acid sequence as shown in SEQ ID NO: 2 or being encoded by a nucleic acid sequence as shown in SEQ ID NO: 1. Moreover, variants of said sequences shall be encompassed which are at least 70%, at least 80%, at least 90%, at least 95%, at least 98% or at least 99% identical to the amino acid sequence shown in SEQ ID NO: 2 or to a protein encoded by the nucleic acid sequence as shown in SEQ ID NO: 1. The percent identity values are, preferably, calculated over the entire amino acid or nucleic acid sequence region. A series of programs based on a variety of algorithms is available to the skilled worker for comparing different sequences. In this context, the algorithms of Needleman and Wunsch or Smith and Waterman give particularly reliable results. To carry out the sequence alignments, the program PileUp (J. Mol. Evolution., 25, 351-360, 1987, Higgins, CABIOS, 5 1989: 151-153) or the programs Gap and BestFit (Needleman 1970, J. Mol. Biol. 48; 443-453; Smith 1981, Adv. Appl. Math. 2; 482-489), which are part of the GCG software packet (Genetics Computer Group, 575 Science Drive, Madison, Wis., USA 53711, 1991), are to be used. The sequence identity values recited above in percent (%) are to be determined, preferably, using the program GAP over the entire sequence region with the following settings: Gap Weight: 50, Length Weight: 3, Average Match: 10.000 and Average Mismatch: 0.000, which, unless otherwise specified, shall always be used as standard settings for sequence alignments. Such homologous variants are, preferably, BMP4 orthologs from other species and, thus, exhibit the same biological properties as BMP4.

BMP4 as used herein refers, preferably, to the protein. The BMP4 protein can be either purified or obtained by recombinant manufacture. However, also envisaged by the present invention is the use of a nucleic acid encoding the BMP4 from which the BMP4 protein can be transcribed. Accordingly, the present invention by referring to BMP4 also encompasses expression polynucleotides comprising BMP4 encoding nucleic acids, preferably, expression cassettes which can be stably integrated into a host cell or expression vectors which allow for transient expression of BMP4 as well as for viral vectors to be used for gene therapeutic approaches. Such expression vectors may be introduced into host cells which are subsequently transferred into or placed adjacent to the neuroblastoma. Alternatively, the expression polynucleotides may be introduced in either cells of the neuroblastoma itself or other cells of the subject. It is to be understood that expression of BMP4 in such expression polynucleotides shall be, preferably, controlled by a promoter which is specifically active in the respective cell type, a constitutively active promoter or an inducible promoter. Suitable promoters are well known in the art and include, e.g., the human CMV promoter or tetracycline inducible promoters.

BMP4 will be applied in the method of the present invention as a pharmaceutical composition. It can be formulated as a pharmaceutically acceptable salt. Acceptable salts comprise acetate, methylester, HCl, sulfate, chloride and the like. The BMP4 comprising pharmaceutical compositions are, preferably, administered topically or systemically. Suitable routes of administration conventionally used for drug administration are oral, intravenous, or parenteral administration as well as inhalation.

The pharmaceutical composition comprising BMP4, preferably, further comprises a pharmaceutically acceptable carrier. The said carrier must be pharmaceutically acceptable in the sense of being compatible with the other ingredients of the formulation and being not deleterious to the recipient thereof. The pharmaceutical carrier employed may be either a solid, a gel or a liquid. Examples of solid carriers are lactose, terra alba, sucrose, talc, gelatin, agar, pectin, acacia, magnesium stearate, stearic acid and the like. Exemplary of liquid carriers are phosphate buffered saline solution, syrup, oil such as peanut oil and olive oil, water, emulsions, various types of wetting agents, sterile solutions and the like. Similarly, the carrier or diluent may include time delay material well known to the art, such as glyceryl mono-stearate or glyceryl distearate alone or with a wax. Said suitable carriers comprise those mentioned above and others well known in the art, see, e.g., Remington's Pharmaceutical Sciences, Mack Publishing Company, Easton, Pa.

The pharmaceutical composition may also further comprise a diluent. The diluent shall not affect the pharmaceutical activity of the combination. Examples of such diluents are distilled water, physiological saline, Ringer's solutions, dextrose solution, and Hank's solution. In addition, the pharmaceutical composition may also include other carriers, adjuvants, or nontoxic, nontherapeutic, nonimmunogenic stabilizers and the like.

A "therapeutically effective dose" as used herein refers to an amount of BMP4 to be used in a pharmaceutical composition of the present invention which prevents, ameliorates or treats the symptoms accompanying a disease or condition referred to in this specification. Therapeutic efficacy and toxicity of such compounds can be determined by standard pharmaceutical procedures in cell cultures or experimental animals, e.g., ED50 (the dose therapeutically effective in 50% of the population) and LD50 (the dose lethal to 50% of the population). The dose ratio between therapeutic and toxic effects is the therapeutic index, and it can be expressed as the ratio, LD50/ED50.

The dosage regimen for BMP4 in the method of the present invention will be determined by the attending physician and other clinical factors; preferably in accordance with any one of the above described methods. As is well known in the medical arts, dosages for any one patient depends upon many factors, including the patient's size, body surface area, age, the particular compound to be administered, sex, time and route of administration, general health, and other drugs being administered concurrently. Progress can be monitored by periodic assessment. A typical dose can be, for example, in the range of 1 to 1000 µg; however, doses below or above this exemplary range are envisaged, especially considering the aforementioned factors. Generally, the regimen as a regular administration of the pharmaceutical composition should be in the range of 1 µg to 10 mg units per day. If the regimen is a continuous infusion, it should also be in the range of 1 µg to 10 mg units per kilogram of body weight per minute, respectively. Progress can be monitored by periodic assessment. BMP4 pharmaceutical compositions referred to herein are administered at least once in order to treat or ameliorate or prevent a disease or condition recited in this specification. However, the said pharmaceutical compositions may be administered more than one time, for example from one to four times daily up to a non-limited number of days.

Advantageously, it has been found in the studies underlying the present invention that BMP4 can be efficiently applied for the treatment of neuroblastoma. Specifically, neuroblastoma tumors were induced in nude mice. 21 days after BMP4 application, the neuroblastoma tumors found in BMP4-treated mice differed significantly in weight compared to those found in untreated control mice. BMP4 abolished by prevention or treatment neuroblastoma formation in nude mice. Thus, it was surprisingly found that a bone morphogenetic protein can act as an efficient anti-tumor drug. Moreover, neuroblastoma related tumors can also be treated by BMP4 using the method of the present invention. Preferably, said neuroblastoma related tumors are nephroblastoma, hepatoblastoma, retinoblastoma, sarcoma, PNET or ependymoma. Like neuroblastoma, these tumors are embryonic childhood tumors.

In the following, particular preferred embodiments of the method of the present invention are described. The definitions and explanations of the terms made above apply mutatis mutandis.

In a preferred embodiment of the method of the present invention, said BMP4 is applied together with chemotherapy. In a more preferred embodiment of the method of the present invention, said chemotherapy is selected from the group consisting of: paclitaxel, docetaxel, vincristine, vindesine, dacarbazine, ifosfamide, etoposide, topotecane, cyclophosphamide, TRAIL, methotrexate, epirubicine, doxurubicine, daunorubicin, idarubicin, epirubicin, mitoxantrone, ellipticine, camptothecin, cisplatin, carboplatin, taxotere, gemcitabine, epothilone B, all-trans retinoic acid, 13-cis retinoic acid, 5-aza-deoxycytidine, 5-aza-cytidine, valproic acid, SAHA, depsipeptide, MS-275 and other histone deacetylase inhibitors, trastuzumab, imatinib, bortezomib.

In a further preferred embodiment of the method of the present invention, said BMP4 is applied together with radiation therapy.

It is to be understood that the aforementioned preferred embodiments may also be combined with each other present, i.e. a combination of radiation therapy and chemotherapy may be additionally applied to the subject to which the method of the present invention shall be applied.

The present invention, in principle, also contemplates the use of BMP4 for the preparation of a pharmaceutical composition treating or preventing neuroblastoma or a neuroblastoma related disease as specified elsewhere in the description in a subject.

The definitions and explanations of the terms made above apply *mutatis mutandis*.

Preferably, said BMP4 is to be administered in combination with a chemotherapeutic agent. More preferably, said chemotherapeutic agent is selected from the group consisting of paclitaxel, docetaxel, vincristine, vindesine, dacarbazine, ifosfamide, etoposide, topotecane, cyclophosphamide, TRAIL, methotrexate, epirubicine, doxurubicine, daunorubicin, idarubicin, epirubicin, mitoxantrone, ellipticine, camptothecin, cisplatin, carboplatin, taxotere, gemcitabine, gemcitabine, epothilone B, all-trans retinoic acid, 13-cis retinoic acid, 5-aza-deoxycytidine, 5-aza-cytidine, valproic acid, SAHA, depsipeptide, MS-275 and other histone deacetylase inhibitors, trastuzumab, imatinib, bortezomib.

Also preferably, said BMP4 is to be administered in combination with a radiation.

All references cited in this specification are herewith incorporated by reference with respect to their entire disclosure content and the disclosure content specifically mentioned in the specification.

The FIGURE show:

FIG. 1: Tumor weight 21 days after treatment with BMP4 is compared to an untreated control (C).

The following Examples merely illustrate the present invention. They shall, whatsoever, not be construed as to limit its scope of protection.

EXAMPLE

BMP4 Represses Neuroblastoma Formation and Growth In Vivo

BE(2)-C neuroblastoma cells (ECACC) were pre-treated in vitro for 48 h with 100 ng/ml BMP4 (Acris), harvested and evaluated for number and viability by coulter counter measurement. $10^6$ viable BE(2)-C were implanted subcutaneously into the flanks of nude mice. BMP4 delivery in vivo was polymer-based. Heparin acrylic beads (Sigma) were incubated in 0.1% BSA (Sigma) or 100 ng/ml BMP4 for 1 h at 37° C., rinsed and implanted. 21 d after implantation, both NB formation and growth were evaluated.

Tumor formation was observed in all BSA-treated animals (n=3). In BMP4-treated animals (n=2), tumor formation was observed in one animal. The tumor size was significantly higher in BSA-treated controls compared with BMP4-treated animals (5.6 g±0.8 versus 0.6 g±0.6; P=0.0009, unpaired Student's t-test performed with SigmaPlot 9.0). These results were confirmed by a second independently carried out experiment (FIGURE and data not shown). In conclusion, BMP4 represses neuroblastoma formation and growth in vivo.

The invention claimed is:

1. A method for treating or for abolishing the progression of neuroblastoma comprising administering to a subject a therapeutically effective amount of bone morphogenetic protein 4 (BMP4) protein.

2. The method of claim 1, wherein said BMP4 protein is administered together with chemotherapy.

3. The method of claim 1, wherein said BMP4 protein is administered together with paclitaxel, doxetaxel, vincristine, vindesine, dacarbazine, ifosfamide, etoposide, topotecane, cyclophosphamide, TRAIL, methotrexate, epirubicine, doxurubicine, daunrubicin, idarubicin, epirubicin, mitoxantrone, ellipticine, camptothecin, cisplatin, carboplatin, taxotere, gemcitabine, epothilone B, all-trans retinoic acid, 13-cis retinoic acid, 5-aza-deoxycytidine, 5-aza-cytidine, valproic acid, SAHA, depsipeptide, MS-275 and/or other histone deacetylase inhibitors, trastuzumab, imatinib, or bortezomib.

4. The method of claim 1, wherein said BMP4 protein is administered together with radiation therapy.

5. The method of claim 1, wherein said neuroblastoma is associated with MYCN gene amplification.

6. The method of claim 1, wherein said subject is a human.

* * * * *